United States Patent [19]

Simpson et al.

[11] 4,411,055

[45] Oct. 25, 1983

[54] VASCULAR GUIDING CATHETER ASSEMBLY AND VASCULAR DILATING CATHETER ASSEMBLY AND A COMBINATION THEREOF AND METHODS FOR MAKING THE SAME

[75] Inventors: John B. Simpson, Menlo Park; Edward W. Robert, Cupertino, both of Calif.

[73] Assignee: Advanced Cardiovascular Systems, Inc., Mt. View, Calif.

[21] Appl. No.: 291,233

[22] Filed: Aug. 10, 1981

Related U.S. Application Data

[60] Division of Ser. No. 151,175, May 19, 1980, Pat. No. 4,323,071, which is a continuation-in-part of Ser. No. 123,713, Feb. 21, 1980, abandoned, which is a continuation of Ser. No. 899,061, Apr. 24, 1978, abandoned.

[51] Int. Cl.³ .................. B23P 11/02; B29C 23/00
[52] U.S. Cl. ............................... 29/447; 264/573
[58] Field of Search ........... 264/230, 521, 573, 565, 264/566, 567, 570, 571; 128/214.4, 348, 349 R; 29/447

[56] References Cited

U.S. PATENT DOCUMENTS

| | | | |
|---|---|---|---|
| 2,936,491 | 5/1960 | Hamlin | 264/230 |
| 3,833,003 | 9/1979 | Tarrico | 128/214.4 |
| 3,861,942 | 1/1975 | Glover et al. | 128/214.4 |
| 4,104,394 | 8/1978 | Okita | 264/230 |
| 4,195,637 | 4/1980 | Gruntzig et al. | 128/348 |

*Primary Examiner*—Ervin M. Combs
*Assistant Examiner*—Steven E. Nichols
*Attorney, Agent, or Firm*—Flehr, Hohbach, Test, Albritton & Herbert

[57] ABSTRACT

Guiding catheter assembly having a first tubular member formed of a material which has a low coefficient of friction and a second tubular member encasing said first tubular member so that the first tubular member fits tightly within said second tubular member. The second tubular member is formed of an irradiated modified polyolefin which is flexible but which has a greater rigidity than the said first tubular member so as to provide the guiding catheter assembly with the desired rigidity to permit manuevering of the same. The combined first and second tubular members have proximal and distal ends with the distal ends having a bend therein permitting engagement in a vascular structure. A fitting is mounted on the proximal ends through which a dilating catheter assembly can be inserted into the guiding catheter assembly.

Dilating catheter assembly having first and second tubular members formed of a flexible irradiated modified polyolefin. The first tubular member is encased within said second tubular member. The combined first and second tubular members have proximal and distal ends. The second tubular member has formed therein near the distal end a distensible or inflatable annular portion. The second tubular member has a passage formed therein extending from the proximal end into the inflatable annular portion so that the inflatable annular portion can be inflated and deflated through the passage. Fittings are provided on the proximal ends of the first and second tubular members so that the inflatable annular portion of the second tubular member can be inflated and deflated independently from fluid infusion or pressure measurements through the first tubular member.

Method for forming a guiding catheter assembly by providing a first tubular member formed of a material which has a low coefficient of friction. A second tubular member formed of a heat-shrinkable material is provided and the first tubular member is inserted therein. Heat is applied to the irradiated modified polyolefin material to cause it to tightly encase the first tubular member and to provide the first tubular member with additional rigidity to provide a catheter assembly which has sufficient rigidity to permit manuevering of the same.

6 Claims, 21 Drawing Figures

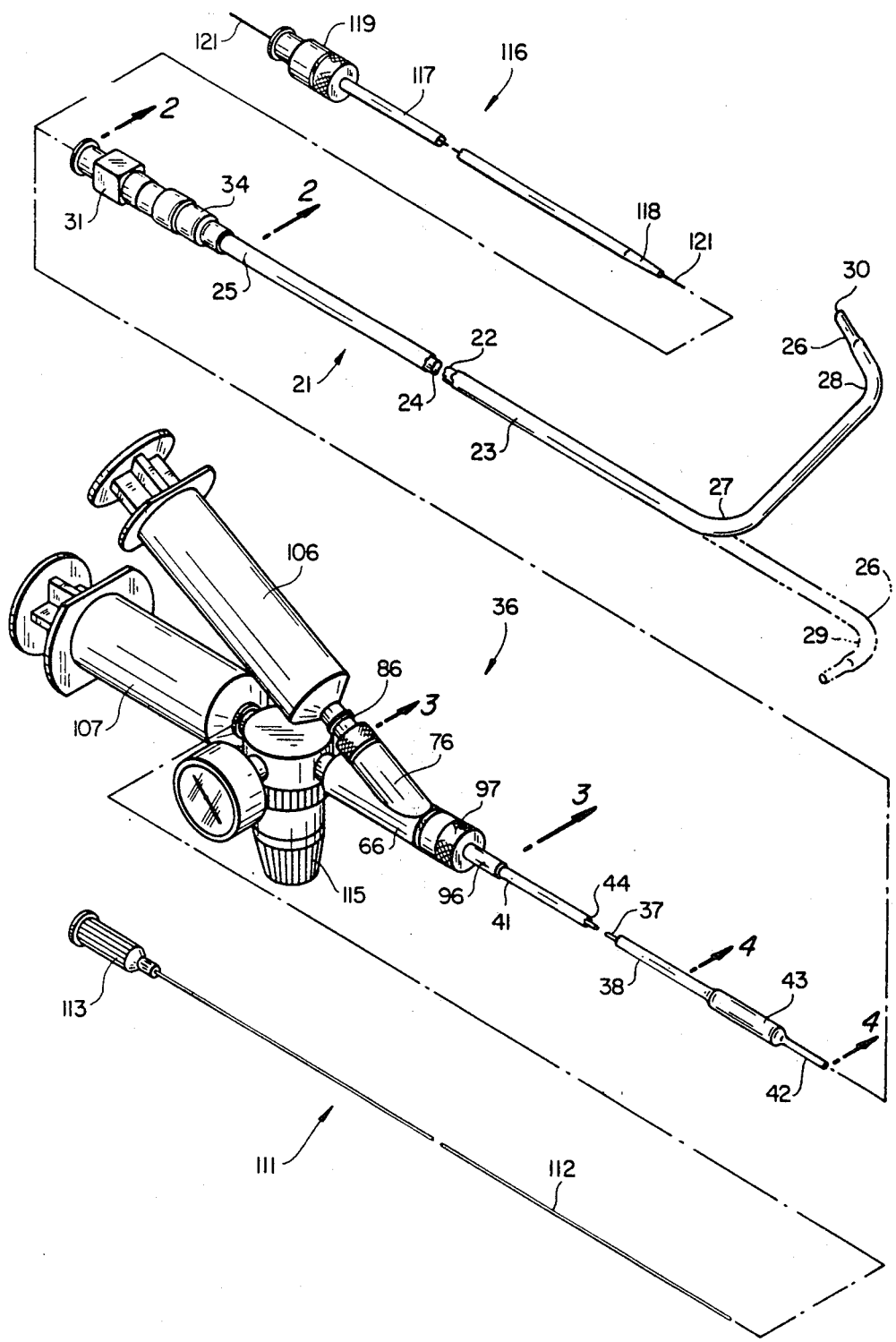
FIG_1

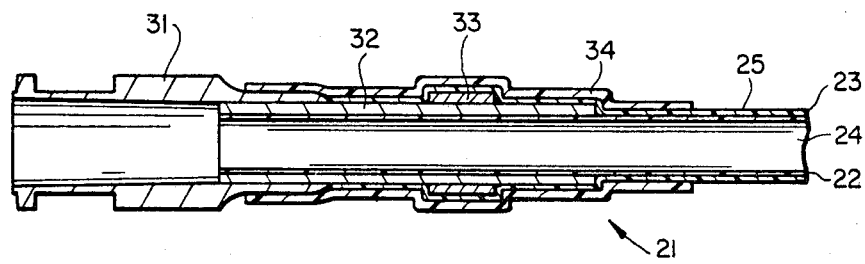
FIG__2
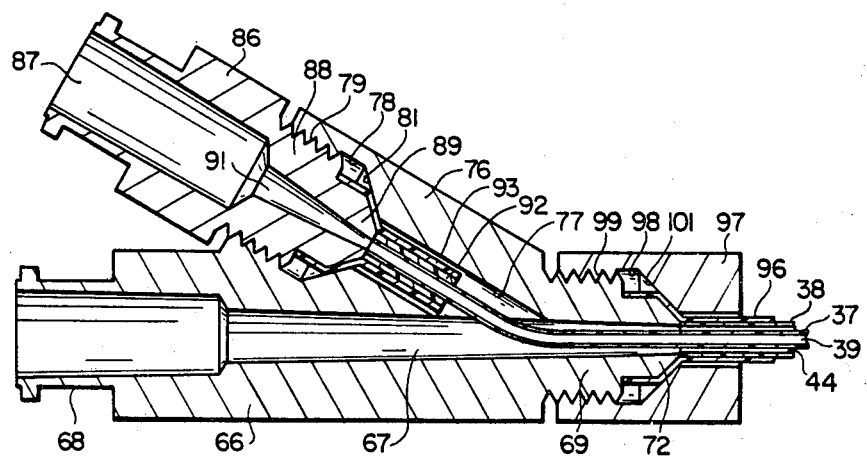
FIG__3
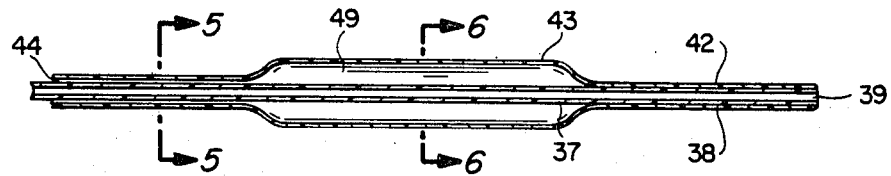
FIG__4
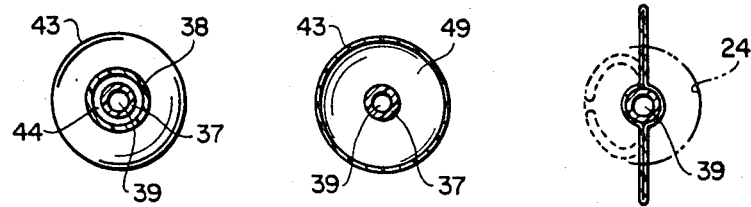
FIG__5  FIG__6A  FIG__6B

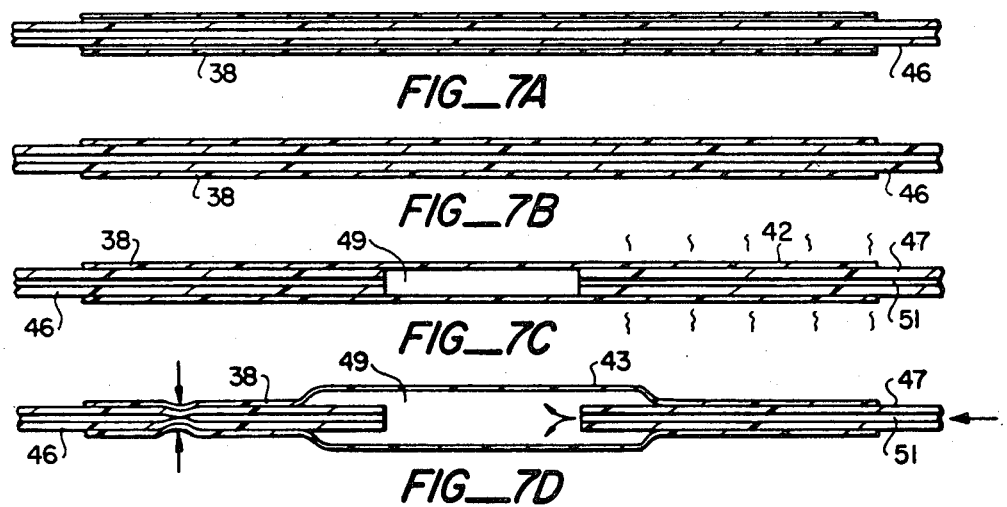
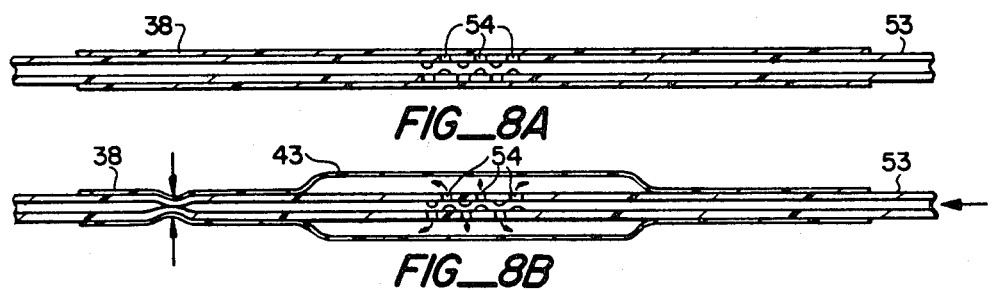
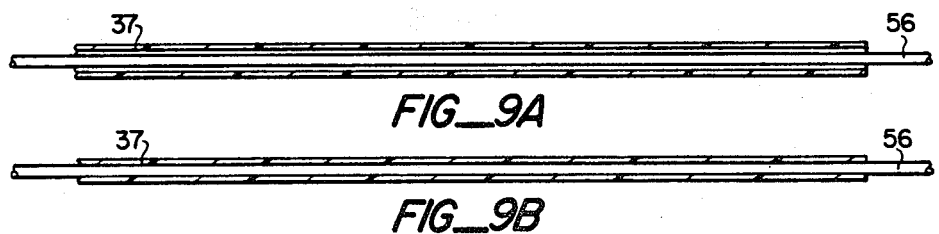
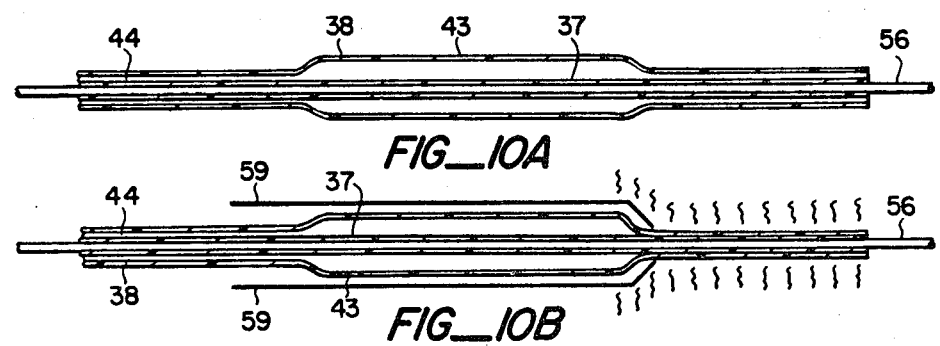

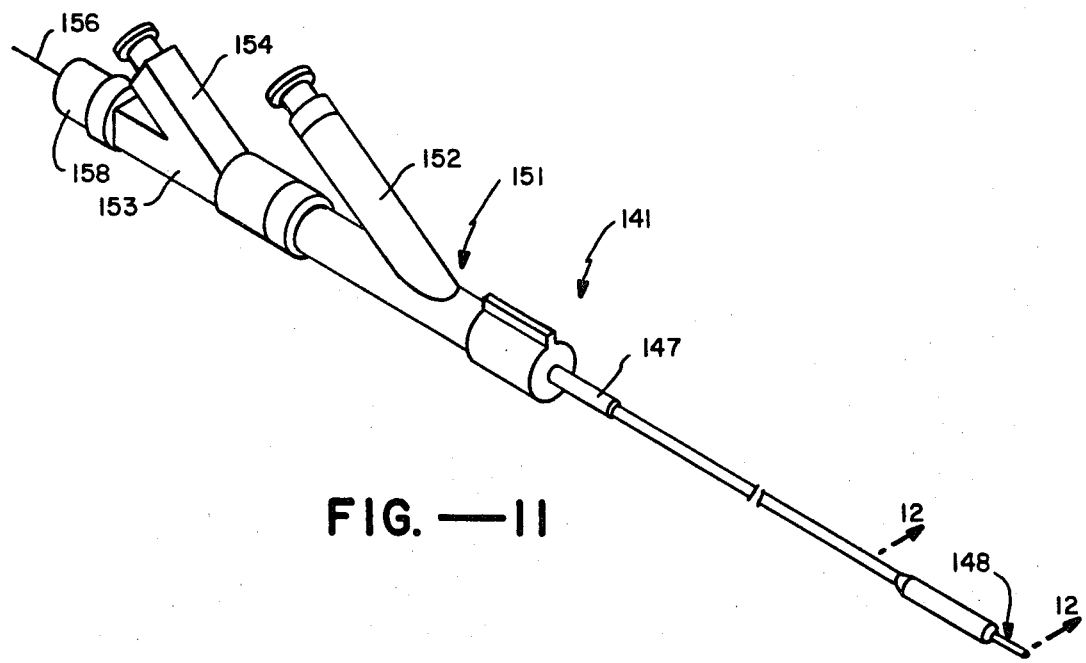
FIG.—11
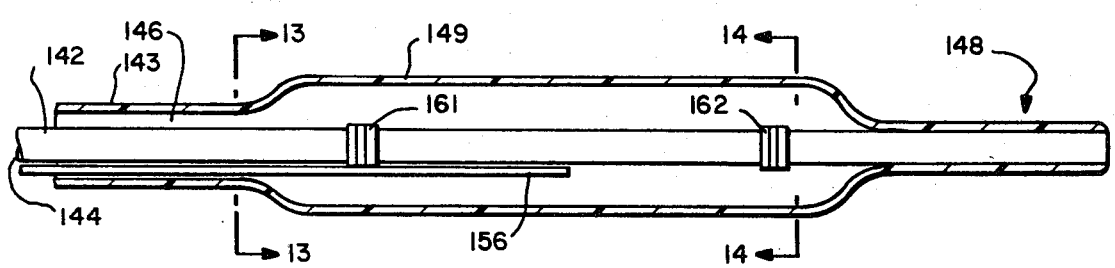
FIG.—12
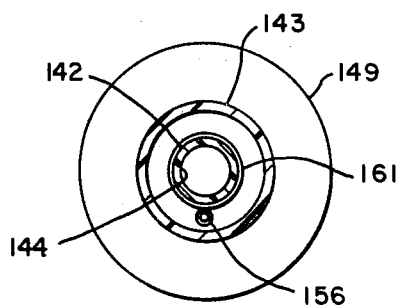
FIG.—13
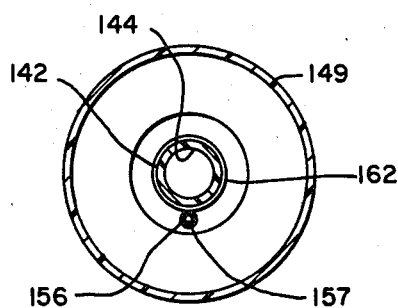
FIG.—14

VASCULAR GUIDING CATHETER ASSEMBLY AND VASCULAR DILATING CATHETER ASSEMBLY AND A COMBINATION THEREOF AND METHODS FOR MAKING THE SAME

This is a division of application Ser. No. 151,175, filed May 19, 1980, now U.S. Pat. No. 4,323,071, which is a continuation-in-part of application Ser. No. 123,713, filed Feb. 21, 1980, now abandoned, which is a continuation of application Ser. No. 899,061, filed on Apr. 24, 1978, now abandoned.

BACKGROUND OF THE INVENTION

As disclosed in the following three references:
1. Grüntzig, A.: Die perkutane transluminale Rekanalisation chronischer Arterienverschlüsse mit einer neuen Dilationstechnik; p. 50. Baden-Baden, 1977.
2. Grüntzig, A., H. H. Riedhammer, M. Turina, Rutishauer W. Verh. Dtsch. Ges. Kreislaufforschg. 1967, 42, 282.
3. Grüntzig, A., R. Myler, E. Hanna, Turina M. Abstracts Circulation. 1977, 56, 84.

a technique has been developed for percutaneous transluminal coronary angioplasty. This technique consists of a catheter system introduced via the femoral artery under local anesthesia. A preshaped guiding catheter is positioned into the orifice of the coronary artery and through this catheter a second dilation catheter is advanced into the branches of the coronary artery. The dilation catheter has an elliptical-shaped distensible balloon portion near the tip which can be inflated and deflated. After traversing the stenotic lesion of the coronary artery, the distensible portion is inflated with fluid which compresses the atherosclerotic material in a direction generally perpendicular to the wall of the vessel thereby dilating the lumen of the vessel. Peripheral arterial lesions treated by this technique have demonstrated by morphological studies that the atheroma can be compressed leaving a smooth luminal surface noted at the time of restudy. The patency rate two years following dilation of iliac and femoropopliteal atherosclerotic lesions was greater than 70%. The continued success of this technique could greatly widen the horizons for coronary angiography and provide another treatment for patients with angina pectoris.

The guiding and dilating catheters utilized by Gruntzig in his work have been more or less hand made. They have been difficult and expensive to fabricate and for that reason it has been very difficult to obtain an adequate supply of the same. There is therefore a need for a new and improved guiding and dilation catheters and methods for making the same.

SUMMARY OF THE INVENTION AND OBJECTS

To perform coronary percutaneous transluminal angioplasty, vascular guiding and dilating catheters must be provided. The present invention is directed to a guiding catheter assembly and dilating catheter assembly and methods for making the same so that they have the desired characteristics and so that they can be made uniformly and without undue expense with volume production being possible.

In general, it is an object of the present invention to provide a guiding catheter assembly which has a very low coefficient of friction so that a dilating catheter assembly can be readily inserted into the same.

Another object of the invention is to provide a guiding catheter assembly of the above character which has sufficient rigidity so that it can be readily manuevered.

Another object of the invention is to provide a method for making the guiding catheter assembly which utilizes heat-shrinkable tubing in the form of an irradiated modified polyolefin for providing the additional rigidity required.

Another object of the invention is to provide a dilating catheter assembly which can be readily inserted through the guiding catheter assembly.

Another object of the invention is to provide a dilating catheter assembly of the above character in which an inflatable or distensible balloon-like portion is formed integral with one of the tubular members forming the dilating catheter assembly.

Another object of the invention is to provide a dilating catheter assembly of the above character in which the balloon-like portion can be readily and reliably formed.

Another object of the invention is to provide a dilating catheter assembly of the above character in which the balloon can be readily inflated with a radiographic contrast liquid and can be rapidly deflated.

Another object of the invention is to provide a dilating catheter assembly of the above character which can be readily inflated with a radiographic contrast liquid being flushed out of the balloon as it is being filled.

Another object of the invention is to provide a method for forming the dilating catheter assembly which utilizes heat-shrinkable tubing for the formation of the balloon-like portion and for forming the passage leading to the balloon.

Another object of the invention is to provide a dilating catheter assembly of the above character in which the catheter is formed of an irradiated modified polyolefin tubing.

Another object of the invention is to provide a dilating catheter assembly of the above character in which inner and outer coaxial tubular members are provided and in which a distal pressure seal is formed between the inner and outer tubular members solely by heating the outer heat shrinkable tubular member.

Another object of the invention is to provide a method for making a dilating catheter assembly in which the balloon-like portion can be readily and easily formed.

Another object of the invention is to provide a method for making a dilating catheter assembly which is reliable and which lends itself to quantity production.

Another object of the invention is to provide a method for inflating the balloon of the dilating catheter assembly with a radiographic contrast liquid and venting any air in the balloon out of the balloon by utilizing a separate flow passage for the escape of air.

Additional objects and features of the invention will appear from the following description in which the preferred embodiments are set forth in detail in conjunction with the accompanying drawings.

BRIEF DESCRIPTION OF THE DRAWINGS

FIG. 1 is a perspective view of a dilator, a guiding catheter assembly, a dilating catheter assembly and a balloon flushing tube and showing the manner in which they are used with respect to each other and incorporated into assemblies for performing coronary percutaneous transluminal angioplasty.

FIG. 2 is a cross-sectional view taken along the line 2—2 of the guiding catheter assembly.

FIG. 3 is a cross-sectional view taken along the line 3—3 of the dilating catheter assembly.

FIG. 4 is a cross-sectional view taken along the line 4—4 of the dilating catheter assembly.

FIG. 5 is a cross-sectional view taken along the line 5—5 of FIG. 4.

FIGS. 6A and 6B are taken along the line 6—6 of FIG. 5 and show the balloon in inflated end deflated conditions respectively.

FIGS. 7A, 7B, 7C and 7D illustrate the steps utilized in one method for forming the balloon from the irradiated modified polyolefin tubing utilized for the dilating catheter assembly.

FIGS. 8A and 8B illustrate the steps in another method utilized for forming the balloon on the outer catheter of the dilating catheter assembly.

FIGS. 9A and 9B show the steps utilized in the method for forming the inner catheter of the dilating catheter assembly.

FIGS. 10A and 10B show the steps in the method of inserting the inner tubular member into the outer tubular member having a balloon formed therein and shrinking the distal end of the outer tubular member onto the distal end of the inner tubular member to provide an air-tight adhesive-free seal and providing a flow passage through which fluid can be introduced into the balloon for inflating the same and withdrawing it from the balloon for deflating the same.

FIG. 11 is an isometric view of another embodiment of our dilating catheter assembly incorporating the present invention.

FIG. 12 is a cross-sectional view taken along the line 12—12 of FIG. 11.

FIG. 13 is a cross-sectional view taken from the line 13—13 of FIG. 12.

FIG. 14 is a cross-sectional view taken along the line 14—14 of FIG. 12.

DESCRIPTION OF THE PREFERRED EMBODIMENTS

The guiding catheter assembly 21 shown in FIG. 1 consists of first and second coaxial tubular members 22 and 23. The first tubular member is formed of a material which has an extremely low coefficient of friction as for example TFE Teflon (a tetrafluoroethylene polymer) having a coefficient of friction of approximately 0.02. For the material for the first tubular member, the coefficient of friction can range from as low a value as possible to 0.05. It is also desirable that the material utilized for the first tubular member have a certain amount of flexibility. The first tubular member has a guiding passageway 24 having an internal diameter of approximately 0.075 of an inch. It also can have a suitable wall thickness preferably in the vicinity of 0.004 of an inch. However, these dimensions can vary within the range of approximately ±15% and still be satisfactory.

Although TFE Teflon utilized for the first tubular member was very desirable because it had a very low coefficient of friction, it was found, however, that it was too flexible with thin walls to serve as a guiding catheter because it could not be properly manipulated in the body of the patient. It is for this reason that the second tubular member 23 is provided. This second tubular member is formed of a heat-shrinkable irradiated modified polyolefin supplied by Raychem Corporation of Menlo Park, Calif. The heat shrinkable tubing selected had an internal diameter of 0.120 of an inch which was of a sufficient size so that the first tubular member could be readily inserted into the same. The second tubular member of the assembled first and second tubular members 22 and 23 was then progressively heated along its length in a suitable manner as by a hot air tool to a suitable temperature as for example 120° C. to cause the second or outer tubular member 23 to shrink in a manner well known to those skilled in the art so that it forms a tight seal with respect to the first tubular member 22. Alternatively this can be accomplished by passing the assembled first and second tubular members through a cylindrical heating unit to cause progressive heating of the second tubular member.

The assembly is provided with proximal and distal ends 25 and 26. The distal end is provided with bends to form a shape identical to the standard coronary catheter. A left coronary guiding catheter is formed by providing two bends 27 and 28 of approximately 120°-150° (proximal) and 60°-90° (distal) each in the same direction to provide the bends which are shown in FIG. 1 for a left coronary artery. As soon as the bends 27 and 28 have been formed, the distal end can be cut off to the desired length and thereafter, the distal end can be sanded or smoothed in a suitable manner. An annular recess 30 is formed on the extreme distal end of the tubular member 23. For a right coronary guiding catheter a single bend 29 as shown by the broken lines in FIG. 1 can be provided.

An attachment or fitting 31 is secured to the proximal end of the first and second tubular member in a suitable manner. The attachment or fitting 31 is in the form of a female Luer fitting or attachment having a metal cylindrical extension 32 on which there is crimped a metal band 33. The first or inner tubular member 22 is inserted into the cylindrical extension 32 and the second or outer tubular member 23 is slipped over the cylindrical extension 32 and the band 33. A sleeve 34 also formed of a similar heat-shrinkable tubing is thereafter slid over the outer or second tubular member 23 and the fitting 31. The sleeve 34 is then heated to a suitable temperature as for example 120° C. to cause it to shrink over the fitting 31 and also over the proximal end of the first and second tubular members 22 and 23 to form an excellent leak-proof adhesive-free connection between the parts.

The material which is utilized for the second tubular member 23 has a substantially higher coefficient of friction than the material utilized for the first tubular member 22. However, this is not objectionable since the second tubular member will be inserted into the blood vessel over a wire in a standard percutaneous technique and thus will be lubricated by the blood in the vessel. The use of the guiding catheter assembly will be described in conjunction with the dilating catheter assembly hereinafter described.

The guiding catheter assembly 21 has a suitable length which is tailored to the purpose for which it is used. As for example, when utilizing the same for doing coronary percutaneous transluminal angioplasty on adults, a length of 95-110 cm. is utilized.

The dilating catheter assembly 36 as shown in FIG. 1, consists of first and second tubular members 37 and 38. The first and second tubular members 37 and 38 are formed of heat-shrinkable tubing of the type hereinbefore described manufactured by Raychem Corporation of Menlo Park, Calif. The first tubular member 37 is provided with a flow passage 39 extending the length of the same. The first tubular member 37 is coaxially disposed within the second tubular member in such a manner so that the second tubular member surrounds the first tubular member. The combined first and second tubular members 37 and 38 have a proximal end 41 and a distal end 42. The second tubular member 38 has formed therein a balloon-like or inflatable annular portion 43 near the distal end 42 of the first and second tubular members 37 and 38. An annular flow passage 44 is formed between the second tubular member 38 and extends from the proximal end into the balloon-like or inflatable annular portion 43 to permit the introduction of fluid into the balloon-like portion 43 for inflating the balloon-like portion and for withdrawing fluid from the same for deflating the balloon-like portion.

The method by which the assembly consisting of the first and second tubular members 37 and 38 with the balloon-like portion 43 and the passages 39 and 44 formed therein ismanufactured can be seen by reference to FIGS. 7A through 7D. The second tubular member 38 has an initial inside diameter of 0.065 inches and an initial outside diameter of 0.085 inches. As is well known to those skilled in the art, the manufacture of heat-shrinkable tubing is accomplished by extruding a modified polyolefin to a predetermined size and utilizing high energy ionizing radiation to cause cross-linking of the polymer chains to occur. Thereafter, the tubing is expanded to a suitable ratio such as 2:1. A mandrel 46 in the form of a Teflon tube is inserted into the tubular member 38 as shown in FIG. 7A. The member 38 is then progressively heated as shown in FIG. 7B to shrink the member 38 down onto the mandrel 46 so that it has an inside diameter of approximately 0.058 inches and an outside diameter of 0.072 inches with a wall thickness of 0.007 inches. The steps shown in FIGS. 7A and 7B are only carried out to provide a tubular member 38 of the desired size. Alternatively this can be accomplished by producing initially a heat-shrinkable tubing of the desired size. The mandrel 46 is withdrawn to the position shown in FIG. 7C and another mandrel 47 in the form of a Teflon tube having an outside diameter of 0.054 inches is placed in the distal end 42. The mandrel 46 extends substantially the entire length of the second tubular member 38 which can have a suitable length ranging from 105 to 120 cm. The mandrel 47 is spaced from mandrel 46 to provide a space 49 through which the balloon-like portion 43 is to be formed. The other mandrel 47 serves as a support for supporting the distal end of the second tubular member 38. The second tubular member 38 is then heated to a suitable temperature as for example 120° C. in the vicinity of the ends of the mandrels 46 and 47 facing the space 49 to shrink those portions of the second tubular member 38 onto the mandrels 46 and 47 to form air-tight seals. The portion of the member 38 encircling the space 49 is then heated until the material reaches a temperature beyond its crystalline melting point. With the mandrel 46 sealed at its proximal end, air under pressure is introduced by suitable means such as a syringe (not shown) through the passage 51 into the space 49 in the tubular member 38 to cause the tubular member to expand to form the balloon-like portion 43 as shown in FIG. 7D. By way of example, air under pressure of 4 to 5 p.s.i. was utilized to form the balloon-like portion 43. Other fluids can be utilized if desired.

The balloon-like portion 43 is formed by expanding that portion of the tubing 38 surrounding the space 49 to its elastic limit which generally corresponds to a ratio of 4 or 5 to 1 from the original extruded irradiated tubing size prior to the initial expansion.

The balloon-like portion 43 thus formed preferably has dimensions ranging in length from approximately 1 to 2 centimeters and an outside diameter ranging from 0.120 to 0.140 inches and a wall thickness ranging from 0.002 to 0.004 inches.

Alternatively the balloon-like portion 43 can be formed as shown in FIGS. 8A and 8B. As shown therein, the mandrel 46 can be removed and another mandrel 53 having holes 54 inserted into the distal end. Heat is then applied to the tubular member on opposite ends of the holes 54 to shrink the tubular member 38 so that it forms air-tight seals with the mandrel 38. The proximal end of the member 38 is clamped and air is introduced into the distal end after the member 38 has been heated in the vicinity of the holes to a temperature beyond the crystalline melting point and a balloon-like portion 43 is formed in the manner hereinbefore described. Thereafter, the mandrel 53 can be removed.

The balloon-like portion is permitted to cool to room temperature while the pressure is maintained in the balloon so that the temperature of the material falls below its crystalline melting point to thereby retain a semi-permanent distensible balloon-like portion 43 within the second tubular member adjacent the distal end thereof. After the balloon-like portion has been sufficiently cooled, the Teflon mandrels 46 and 47 are removed to provide a second or outer sheath.

The first or inner tubular member 37 is formed by taking a tube of heat-shrinkable tubing of the type hereinbefore described having an outside diameter of 0.05 and having an inside diameter 0.030 having a suitable length as for example approximately 110 cm. and placing within the same a Teflon coated guide wire (or a Teflon mandrel) 56 having an outside diameter of 0.021 inches as shown in FIG. 9A. The first tubular member 37 with the guide wire 56 therein which serves as a mandrel is heated to a suitable temperature as for example 125° C. and stretched to cause the first tubular member 37 to shrink down onto the guide wire 56 as shown in FIG. 9B.

The assembly which is shown in FIG. 9B is then taken and inserted into the outer sheath or tubular member 38 which is shown in FIG. 10A. It extends beyond both ends of the outer sheath and passes through the balloon portion 43. The balloon-like portion 43 is then covered with a cover 59 of a suitable type such as aluminum foil for protecting the balloon-like portion 43 from heat. Thereafter, the portion of the second tubular member 38 from the balloon-like portion 43 to the distal end is heated to a suitable temperature as for example 125° C. to cause the outer tubular member 38 to shrink tightly onto the first tubular member 37 with the Teflon guide wire or mandrel 56 therein to provide a fluid tight adhesive-free seal between the first and second tubular members 37 and 38. After the material has cooled, the mandrel 56 is removed to provide the construction hereinbefore described that is, a first tubular member 37 with a flow passage 39 therein and a second tubular member 38 coaxial with tubular member 37 with an annular flow passage 44 therein extending from the proximal end into the balloon portion 43.

The proximal ends of the first and second tubular members 37 and 38 as shown in FIG. 3 are inserted into an adapter body 66. The body 66 is formed of a suitable material such as metal or plastic and is provided with a centrally disposed bore 67 which opens through a female Luer type fitting 68. The adapter body 66 is also provided with a threaded cylindrical projection 69 and a generally conical portion 72 which projects beyond the threaded projection 69. The adapter body 66 is provided with a side arm 76 which is provided with a cylindrical bore 77 that extends into the bore 67 at a suitable angle as for example an angle of approximately 30°. A well 78 is formed in the side arm 76 and is provided with an internally threaded portion 79 and a conical-shaped recess 81. As shown particularly in FIG. 3, the first or inner tubular member 37 is placed in contact with a fitting 86. The fitting 86 is provided with a cylindrical bore 87. As can be seen, the fitting 86 is in the form of a conventional female-type Luer fitting. The fitting 86 is provided with a threaded projection 88 which engages the internal threads 79. It is also provided with a conical projection 89 which is adapted to seat against the conical recess 81.

In the construction shown in FIG. 3, the inner tubular member 37 is brought into engagement with the inner end of a conical bore 91 provided in the threaded portion 88 and the conical portion 89 of the fitting 86 and is thus in communication with the cylindrical bore 87. Suitable means is provided with maintaining the flow passage 39 in the first tubular member 37 in communication with the conical bore 91 and consists of a heat-shrinkable tubular member 92 which is secured to the proximal end of the first tubular member 37. Member 92 is provided for the purpose of reinforcing the proximal end of the tubular member 37. Another heat-shrinkable tubular member 93 which has a flared outer end is shrunk onto the tubular member 92 and is fitted onto the conical projection 89 and is firmly held in place by threading of the fitting 86 into the side arm 76.

A heat shrinkable tubular member 96 having a flared outer end is secured to the proximal end of the second tubular member 38. The flared outer end of the tubular member 96 is then positioned over the conical portion 72 of the adapter body 66 and is held in place by a collar 97 which is provided with a well 98 having an internally threaded portion 99 and a conical recess 101 against which the conical projection 72 is adapted to seat to firmly grip the flared portion of the tubular member 96.

First and second syringes 106 and 107 are adapted to be placed in the fittings 86 and 68 as shown particularly in FIG. 1. The syringes 106 and 107 are of a conventional type and therefore will not be described in detail.

After the fittings hereinbefore described have been provided on the proximal end of the first and second tubular members 37 and 38, the distal end can be cut to the proper length and then ground to provide a smooth tapered distal end.

The balloon flushing tube 111 which is also shown in FIG. 1 consists of a long tubular member 112 formed of a suitable material such as stainless steel and having a length ranging from 36 to 40 inches. By way of an example, it can have an outside diameter of 0.020 inch and an internal diameter of 0.10 inch. The tubing 112 has its proximal end connected to a conventional female Luer-type fitting 113 formed of a suitable material such as aluminum. The tubular member 112 can be secured to the fitting 113 by soldering or by a crimp fit.

A dilator 116 which is shown in FIG. 1 is of a conventional type and consists of a flexible tube 117 formed of plastic and having a tapered distal end 118 having an outside diameter of 0.080 inches and an inside diameter of 0.040 inches. A female Luer-type fitting 119 is secured to the proximal end of the tube 117. A flexible Teflon coated guide wire 121 of a conventional type with an outside diameter of 0.038 inches is adapted to be inserted through the dilator 116 as shown.

Use of the guiding catheter 21, the dilating catheter 36 and the balloon flushing tube 111 can now be briefly described as follows. Let it be assumed that it is desired to utilize these devices with a middle-aged patient who has been identified as having a significant narrowing in one of the coronary arteries as for example the left anterior descending coronary artery i.e. the proximal portion of that vessel for which a coronary transluminal dilation is considered advisable.

The patient is brought into a sterile environment and is prepared by sterilizing one of the groins. In preparation for operating upon the patient, the dilating catheter assembly 36 is checked. Normally, the dilating catheter assembly 36 would be supplied with the balloon flushing tube 111 in place. However if this is not the case, the balloon flushing tube 111 can be inserted through the passage 44 until it enters into the balloon 43. A syringe (not shown) filled with a radiographic contrast liquid inserted into the fitting 113 and the fluid is introduced into the balloon 43 to fill the balloon at the same time to flush out any air bubbles which may exist in the balloon or in the passage or lumen 44 leading to and from the balloon. The balloon flushing tube 111 can then be removed and as soon as it is removed, a syringe 107 is placed in the fitting 68 and is filled with a radiographic contrast liquid. The operations thus far described have taken place outside the body of the patient. Before inserting the dilating catheter assembly 36 into the body, the inflation and deflation of the balloon 43 can be readily checked merely by operating the syringe 107. A conventional pressure gauge and pressure regulator 115 are provided associated with the syringe 107 so that one can ascertain and limit the pressure being applied to the balloon 43 to approximately 45 to 80 psi.

When this has been accomplished, the guiding catheter 21 can be inserted into the patient in a standard percutaneous technique. The guiding catheter 21 has been designed so that it can enter into one of either the right or left femoral arteries. In such a technique, a needle is inserted into the femoral artery and the Teflon covered guide wire 121 is inserted through the needle and through the femoral artery into the aorta. The movement of the guide wire and positioning thereof is observed with conventional fluoroscopic techniques. It is positioned so that its tip is generally at the level of the diaphragm of the patient which is essentially half way up the aorta. The dilator 116 is positioned in the guiding catheter assembly 21 so that the flexible tapered tip 118 projects from the distal end of the guiding catheter assembly 21.

The distal end of the guiding catheter assembly 21 is then straightened out and the dilator and the guiding catheter 21 are passed over the guide wire which is already in place and is then introduced into the femoral artery. The guiding catheter is then passed up along the guide wire using the guide wire as a guide to the descending aorta or arch of the aorta. During the time that the guiding catheter assembly is being inserted, the operation is under continuous fluoroscopic control. The dilator carried by the end of the guiding catheter assembly is radiopaque and therefore can be easily visualized radiographically. The guiding catheter is inserted until the distal end of the catheter is at the desired point which will generally be in the ascending portion of the aorta several centimeters from the coronary artery ostium. As soon as the guiding catheter assembly has reached this position, the guide wire and the dilator can be removed from the guiding catheter and the guiding catheter will be aspirated to remove any debris then flushed with radiopaque contrast medium. Thereafter, the catheter can be flushed with a saline solution or contrast medium.

As soon as entry into the blood vessel has been accomplished as hereinbefore described with the guiding catheter assembly 21, the patient can be given intravenous heparin in a standard dose to act as a anticoagulant and to prevent any abnormal thrombosis or blood clot formation on the catheter or in the areas of catheter entry. The guiding catheter assembly 21 can then be filled with a radiographic contrast material such as Renographin 76 and the catheter can be advanced until it engages into the left main coronary ostium which is the artery to be utilized. The positioning of the guiding catheter can be confirmed by one or more injections of the contrasting liquid into the coronary vessel in which fluoroscopic observations are taking place.

As soon as it has been ascertained that the guiding catheter assembly 21 has been properly positioned in the coronary ostium, the dilating catheter assembly 36 can be inserted. To insert the dilating catheter, the balloon 43 is completely deflated as shown in FIG. 6B. When it is deflated, it may assume the position shown by broken lines in FIG. 6B so that the dilating catheter assembly 36 can be readily inserted into the guiding catheter assembly 21. As hereinbefore explained, since the guiding catheter assembly 21 is formed of a first tubular member which is formed of a material having a low coefficient of friction, it is possible to push the dilating catheter assembly 36 through the entire length of the guiding catheter assembly 21 so that it will protrude out of the distal tip of the guiding catheter assembly by suitable distance such as 5 or 6 cm. and protrude into the left main coronary orifice.

Initially the balloon 43 is positioned in one of the closest portions of the vessel the aorta and then gradually under fluoroscopic control is advanced to the point where the narrowing has been previously documented to exist. The balloon is then appropriately positioned in the narrowed portion.

Although it should be possible in all cases to be able to insert the dilating catheter 36 into the guiding catheter assembly without the help of a guide wire, a small guide wire can be utilized if desired. If such is the case, a small guide wire can be inserted through the sidearm 76 and through the first tubular member 37 so it extends just to the distal portion of the dilating catheter assembly 36 or slightly beyond it. If such guide wire is utilized, after the dilating catheter assembly 36 is in position, the small guide wire can be removed and the syringe 106 having a radiographic contrast liquid therein can be mounted on the side arm 76 and small injections of the contrasting liquid can be introduced into the first inner tubular member 37 through the passage 39 to document the position of the distal end of the dilating catheter assembly 36. If desired, the guide wire can be reinserted at any time to be used as an aid in guiding the dilating catheter into the vessel that has previously demonstrated that it is subject to a stenosis or narrowing. As soon as it has been established that the balloon 43 has been positioned within the stenosis, pressure can be applied by the use of the hand syringe 107 to inflate the balloon to a suitable pressure as for example from 3 to 5 atmospheres. The inflation of the balloon can be visualized radiographically because the balloon is filled with a radiographic contrast liquid. By way of example, the balloon would be inflated for a period ranging from 2 to 5 seconds and then deflated rapidly and removed from the stenosis at which time a second coronary contrast injection can be made either through the guiding catheter itself or through the passage 39 of the inner catheter 37.

As far as can be ascertained, the inflation of the balloon causes dilation of the material deposited in the wall of the vessel by causing elongation of the material along the wall and compressing of the material against the wall so that the end result is an increased blood vessel lumen size with increased blood flow to provide an improved oxygen delivery to the jeopardized portion of the heart muscle or myocardium.

The procedure can be repeated as many times as deemed necessary either on the same site or at a stenosis or narrowing in a second vessel. As soon as the necessary dilations have been completed, the dilating catheter assembly 36 can be removed. Thereafter, the guiding catheter assembly 21 can be removed merely by pulling it out of the femoral artery. As soon as the guiding catheter has been removed, the groin is held firmly to prevent any bleeding until clotting has been accomplished. The patient can then be returned to his room and instructed to remain at bed rest with the legs straight and flat for approximately six hours after which normal routine activity can be undertaken by the patient.

It should be appreciated that if desired, a dilating catheter assembly 36 can be provided which only utilizes a single tubular member with a balloon near its distal end. When this is the case, the first tubular member 37 can be omitted, and the tubular member which is utilized can be shrunk down to the final desired size onto mandrels prior to formation of the balloon portion.

Another embodiment of the dilating catheter assembly is shown in FIGS. 11-14. The dilating catheter assembly 141 consists of first and second tubular members 142 and 143. The first and second tubular members 142 and 143 are formed of heat shrinkable material of the type hereinbefore described manufactured by Raychem Corporation of Menlo Park, Calif. The first tubular member 142 is provided with a flow passage 144 extending the length of the same. The first tubular member 137 is coaxially disposed within the second tubular member 143 in such a manner so that the second tubular member surrounds the first tubular member. The sizing of the members 142 and 143 is such that an annular flow passage 146 is provided between the outer surface of the first tubular member 142 and the inner surface of the second tubular member. The combined first and second tubular members 142 and 143 have a proximal end 147 and a distal end 148.

The second tubular member is provided with a distensible or inflatable annular portion or segment 149 which is adjacent the distal end 148. The dilating catheter assembly 141 is manufactured in a manner very similar to that described for the dilating catheter assembly 36. Thus, the outer extremities of the members 142 and 143 are fused or bonded together as shown in FIGS. 11 and 12 to provide a fluid tight seal between the outer extremities of the first and second members 142 and 143. The annular flow passage 146 between the inner surface of the member 143 and the outer surface of the member 142 provides a flow passage which is in communication with the interior of the inflatable annular portion 149 and the proximal end 147.

The proximal end 147 of the combined first and second tubular members 142 and 143 is inserted into an adapter body 151 similar to the adapter body 66 with the principal difference being that the adapter body 66 is formed of metal and the adapter body 151 is formed of plastic. The adapter body 151 is provided with a side arm 152. Another adapter body 153 is mounted on the adapter body 151 and is also provided with a side arm 154. The side arms 152 and 154 are provided with conventional Luer-type fittings.

In order to facilitate filling of the inflatable annular portion 149 with a radiographic contrast liquid, it is desirable to provide some means for permitting the air flushed from the inflatable annular a portion 149 and the passage leading to the annular portion 149 to exit or be vented to the atmosphere. This is accomplished by inserting a flexible tubular member 156 which can be called a flush tube into the flow passage 146 between the first and second tubular members 142 and 143 so that it is in communication with the interior of the distensible annular portion 149 and also extends out of the proximal end 147 of the combined first and second tubular members 142 and 143 and preferably so that it extends out of the adapter bodies of 151 and 153 as shown in FIG. 11. The tubular member or flush wire 156 is provided with a flow passage 157 through which air can readily pass when radiographic contrast medium is introduced into the flow passage 146 through port 154.

It is desirable to have the dilating catheter assembly as small as possible so that it can be readily utilized in human beings. For the same reason it is desirable to make the flush wire or tube as small as possible so that it can fit within a flow passage which is also relatively small. Thus, by way of example, the flush wire can be constructed of a suitable material such as stainless steel and have an inside diameter of 0.004 inches and outside diameter of 0.008 inches.

At the distal end of the dilating catheter assembly, the combined first and second tubular members 142 and 143 are fused and have an outside diameter of 0.035 inches and an inside diameter of 0.023 inches and a wall thickness of 0.006 inches. At the proximal end of the dilating catheter assembly 141, the outer member has an outside diameter of 0.055 inches and an inside diameter 0.043 inches with a wall thickness of 0.006 inches.

The inner or first tubular member throughout has an outside diameter of 0.034 inches and an inside diameter of 0.023 inches and a wall thickness of 0.0055 inches.

It can be seen from the dimensions given, there is sufficient space in the flow passage 146 to permit the passage of the flush wire 156 therethrough.

In order to facilitate placment of the distensible annular portion during use of the dilating catheter assembly, a pair of spaced apart markers 161 and 162 are provided. As shown, the markers 161 and 162 are formed of a metal ribbon which can be gold that is helically wrapped onto the first or inner tubular member 142 in two positions soaced 1.5 cm. apart, and fixed with a small amount of cyanoacylate ester. The two positions correspond generally to the two extremities of the balloon-like portion 149 as shown in FIG. 12. The gold ribbon can have a suitable dimension such as 0.002 inches and width of 0.010 of an inch with five wraps of the same being utilized to provide a marker.

The adapter body is provided with a fitting 158 which is threaded thereon. The fitting 158 carries a resilient siding member (not shown) disposed within the same and having a small hole therein through which the flush wire 166 extends, when the fitting 158 is threaded onto the adapter 153, the resilient sealing member is compressed against the flush wire 156 to form a liquid-tight seal between the flush wire 156 and the fitting 158.

Operation and use of the dilating catheter assembly may now be briefly described as follows: Let it be assumed that the dilating catheter assembly has been assembled in the manner herein described in connection with previous embodiments. The principal difference would be that the markers 161 and 162 would be formed onto the inner tubular member 142 before assembly. After the inner and outer tubular members have been assembled with the adapter 151, the flush wire or tube 156 can be inserted manually through the adapter 151 through the passage 146 until it extends into the annular portion 149 as shown in FIG. 12. The adapter 153 can then be placed on the flush wire or tube 156 inserted into the adapter 151. The fitting 158 can then be positioned onto the flush wire with its sealing member therein and with the flush wire extending therethrough. The fitting 158 is then threaded onto the adapter 153 with the sealing member therein being compressed to form a liquid-tight seal between the flush wire 156 and the fitting 158. The dilating catheter assembly is ready for packaging and is ready for use in this condition with the flush wire 156 in place.

Let is be assumed that it is now desired to use the dilating catheter assembly in connection with procedures to be performed upon a patient. Before use it is desirable to inflate the balloon with a radiographic contrast liquid. This can be accomplished by taking a syringe (not shown) which can be filled with a radiographic contrast liquid and placing the same onto the side arm 154. The side arm 152 is covered with a plug (not shown) to prevent escape of liquid therefrom. The syringe is then operated to cause the radiographic contrast liquid in the syringe to pass through the passage 146 into the distensible annular portion 159 to inflate the same. As the radiographic contrast liquid enters the passage 146 and the annular portion 149, air within the passage 146 and the annular portion 149 is flushed out and is permitted to escape through the flush wire 156 to be vented to the atmosphere. This procedure continues until the annular portion 149 has been completely filled and is free of air. Since the annular portion 149 is outside of the body, the annular portion 149 can be readily examined visually to ascertain whether or not there are any air bubbles remaining. The use of the flush wire 156 ensures that all air within the balloon portion 149 can escape and be vented readily. In addition, the flush wire 156 facilitates rapid filling of the distensible annular portion 149.

If it is ascertained that the annular portion 149 has been properly inflated and all air has been flushed from the dilating catheter assembly, the radiographic contrast liquid may be withdrawn from the distensible annular portion to deflate or collapse of the same. Thereafter, the adapter 143 is removed along with the flush wire 156.

The dilating catheter assembly can be placed in a guiding catheter assembly of the type hereinbefore described where a seal is formed around the dilating catheter assembly while it is in the guiding catheter assembly to prevent leakage of blood out around the guiding catheter assembly and also to permit the pressure of radiographic contrast liquids to be measured in the guiding catheter during the dilation procedure. The remainder of the procedure is the same as hereinbefore described with the previous embodiment.

It is apparent from the foregoing that there has been provided a vascular dilating catheter and an assembly thereof and method for making the same which makes it possible to fabricate the same utilizing quantity production techniques. The construction of the guiding catheter assembly and the dilating catheter assembly is such that the methods utilized take advantage of heat-shrinkable tubing. The guiding catheter assembly has an interior surface which has a very low coefficient of friction so that the dilating catheter assembly can be readily inserted therethrough. In addition, the guiding catheter assembly has sufficient rigidity so that it can be readily manuevered. The dilating catheter assembly is provided with an inflatable annular portion which is formed integral therewith which can be readily inflated and deflated through an annular passage independently from fluid infusion or pressure measurements through the inner catheter.

What is claimed is:

1. In a method for forming a dilating catheter assembly, providing first and second flexible tubular members formed of a heat-shrinkable material, the second tubular member having a diameter greater than that of the first tubular member, the first and second tubular members having proximal and distal ends, heating a portion of the second tubular member adjacent the distal end to a temperature above a predetermined temperature and introducing a fluid under pressure to cause expansion of said portion to form an inflatable annular portion and cooling the same while under pressure to maintain said inflatable annular portion in said second tubular member, inserting a mandrel into the first tubular member, heating the first tubular member to shrink it onto the mandrel, inserting the first tubular member with the mandrel therein into the second tubular member, heating the distal end of the second tubular member to cause it to shrink onto the first tubular member with the mandrel therein to form an adhesive-free seal between the distal ends of the first and second tubular member, and providing a fitting on the proximal ends of the first and second tubular members, said fitting having passages which are in communication with a passage in the first tubular member extending therethrough from the fitting to the distal end and in communication with a passage in the second tubular member extending from the fitting into the inflatable annular portion.

2. In a method for forming a dilating catheter assembly, providing first and second flexible tubular members formed of a heat-shrinkable material, the second tubular member having a diameter greater than that of the first tubular member, the first and second tubular members having proximal and distal ends, heating a portion of the second tubular member adjacent the distal end to a temperature above a predetermined temperature and introducing a fluid under pressure to cause expansion of said portion to form an inflatable annular portion and cooling the same while under pressure to maintain said inflatable annular portion in said second tubular member, inserting a mandrel into the first tubular member, heating the first tubular member to shrink it onto the mandrel, inserting the first tubular member with the mandrel therein into the second tubular member, heating the distal end of the second tubular member to cause it to shrink onto the first tubular member with the mandrel therein to form an adhesive-free seal between the distal ends of the first and second tubular member, and providing a fitting on the proximal ends of the first and second tubular members which are in communication with the passage in the first tubular member extending therethrough and in communication with the passage in the second tubular member extending from the fitting into the inflatable annular portion.

3. In a method for forming a dilating catheter assembly, providing first and second flexible tubular members, the second tubular member having a diameter greater than that of the first tubular member, the first and second tubular members having proximal and distal ends, heating a portion of the second tubular member adjacent the distal end to a temperature above the crystalline melting point of the material and introducing a fluid under pressure to cause expansion of said portion to form an inflatable annular portion, cooling the inflatable annular portion while it is under pressure to retain the inflatable annular portion, inserting the first tubular member into the second tubular member so it extends therethrough, forming a fluid-tight seal between the distal ends of the first and second tubular members, providing a fitting on the proximal ends of the first and second tubular members and with passages which are in communication with the passage within the first tubular member and the passage between the first tubular member and the second tubular member and in communication with the inflatable annular portion.

4. A method as in claim 3 together with the step of providing first and second tubular members formed of a heat-shrinkable material and wherein the formation of the seal between the distal ends of the first and second tubular members is accomplished by heat-shrinking the second tubular member onto the first tubular member.

5. A method as in claim 4 together with the step of inserting a flush wire into the passage in communication with the inflatable annular portion to facilitate the venting of any air in the inflatable annular portion when the inflatable annular portion is filled with a radiographic contrast liquid.

6. In a method for forming a dilating catheter assembly, providing a tubular member formed of plastic material, providing a first tubular member formed of plastic material, providing a second flexible tubular member formed of a heat-shrinkable plastic material, the second tubular member having a diameter greater than that of the first tubular member, the first and second tubular members having proximal and distal ends, heating a portion of the second tubular member adjacent the distal end to a temperature above a predetermined temperature and introducing a fluid under pressure to cause expansion of said portion to form an inflatable annular portion and cooling the same while under pressure to maintain said inflatable annular portion in said second tubular member, inserting the first tubular member into the second tubular member, heating the distal end of the second tubular member to cause it to shrink onto the first tubular member to form an adhesive-free seal between the distal ends of the first and second tubular members, and providing a fitting on the proximal ends of the first and second tubular members, said fitting having passages which are in communication with a passage in the first tubular member extending therethrough from the fitting to the distal end and in communication with a passage in the second tubular member extending from the fitting into the inflatable annular portion.

* * * * *